(12) United States Patent
Frick

(10) Patent No.: US 7,128,300 B2
(45) Date of Patent: Oct. 31, 2006

(54) STAND FOR A SURGICAL MICROSCOPE

(75) Inventor: Roman Frick, Nofels (AT)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 87 days.

(21) Appl. No.: 10/603,509

(22) Filed: Jun. 25, 2003

(65) Prior Publication Data
US 2004/0104328 A1 Jun. 3, 2004

(30) Foreign Application Priority Data
Dec. 3, 2002 (DE) .......................... 202 18 693 U

(51) Int. Cl.
F16M 13/00 (2006.01)

(52) U.S. Cl. .................. 248/418; 248/125.7; 248/415; 248/676

(58) Field of Classification Search ................ 248/121, 248/122.1, 125.7, 415, 145.7, 289.11, 288.51, 248/418, 646, 658, 676
See application file for complete search history.

(56) References Cited

U.S. PATENT DOCUMENTS

| 4,548,373 | A | * | 10/1985 | Komura | 248/122.1 |
| 4,907,467 | A | * | 3/1990 | Toyoda et al. | 74/490.03 |
| 5,667,186 | A | * | 9/1997 | Luber et al. | 248/550 |
| 5,814,960 | A | * | 9/1998 | Ookura et al. | 318/568.11 |
| 5,908,979 | A | * | 6/1999 | Miyamae | 73/12.14 |
| 6,035,228 | A | * | 3/2000 | Yanof et al. | 600/429 |
| 6,679,470 | B1 | * | 1/2004 | Metelski | 248/676 |
| 6,871,828 | B1 | * | 3/2005 | Frick et al. | 248/415 |
| 2002/0185583 | A1 | * | 12/2002 | Metelski | 248/676 |
| 2004/0104328 | A1 | * | 6/2004 | Frick | 248/415 |

FOREIGN PATENT DOCUMENTS

DE 102 23 166 A1 12/2002

* cited by examiner

Primary Examiner—Richard E. Chilcot, Jr.
Assistant Examiner—Tan Le
(74) Attorney, Agent, or Firm—Hodgson Russ LLP

(57) ABSTRACT

A stand (3) for a surgical microscope comprising at least one vertical rotary bearing (4). A pivot arm (5) is mounted rotatably in the rotary bearing (4). An electromagnetic brake (6) for blocking the pivoting motion of the pivot arm (5) in the rotary bearing (4) is provided. A mechanical brake (7) with adjustable braking force is additionally present for braking the pivot arm (5) in the rotary bearing (4).

5 Claims, 3 Drawing Sheets

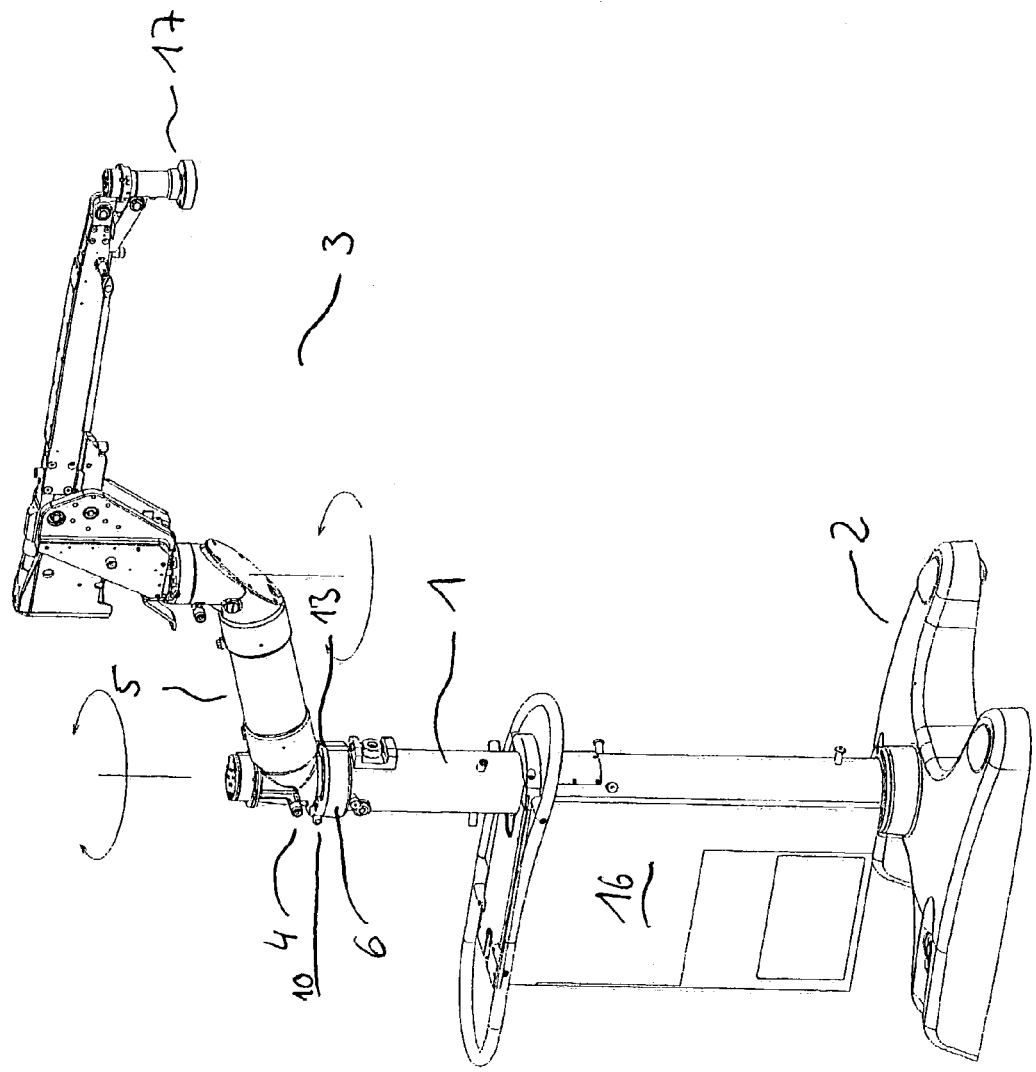

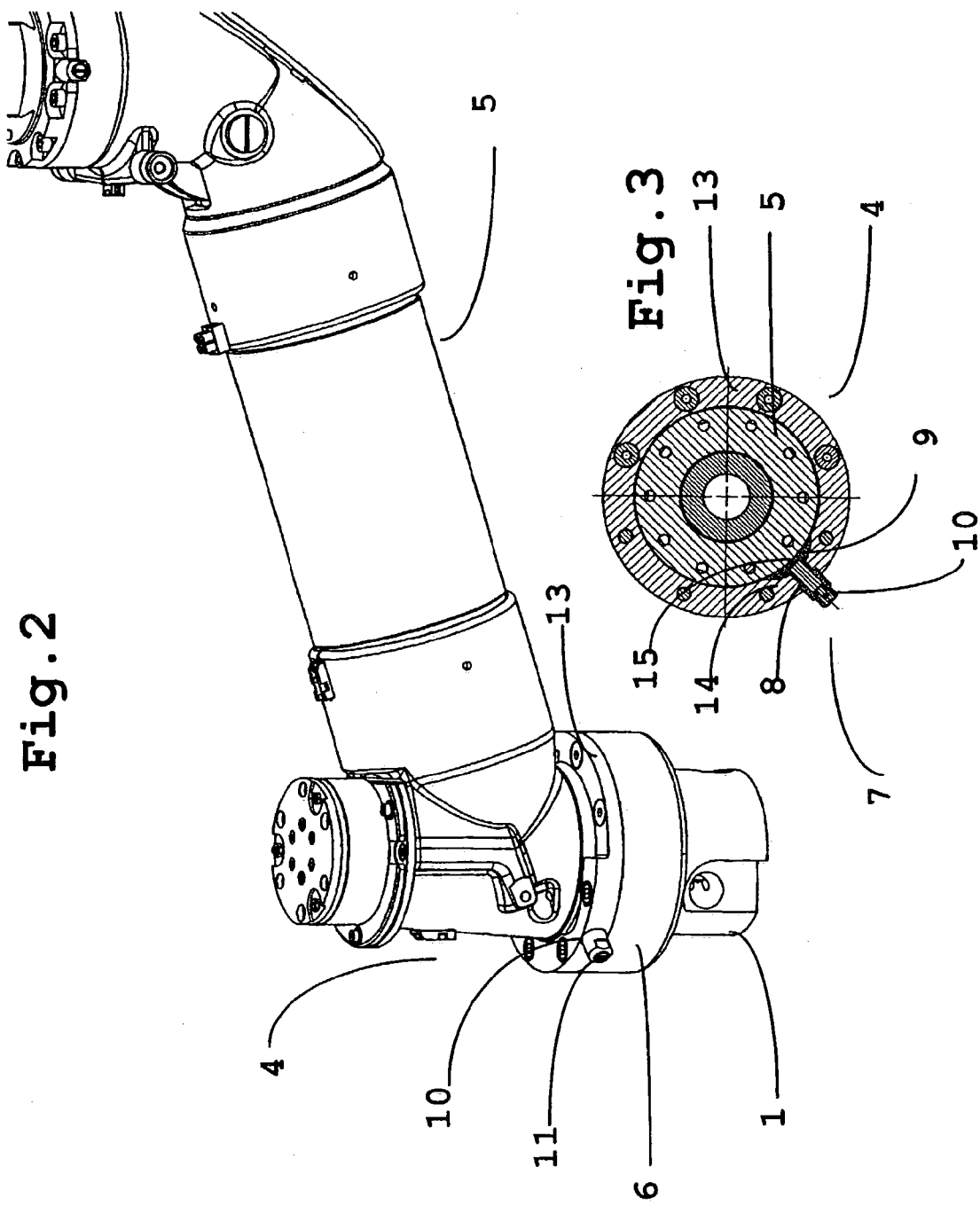

STAND FOR A SURGICAL MICROSCOPE

CROSS REFERENCE TO RELATED APPLICATIONS

This application claims priority of the German utility model application 202 18 693.8 filed Dec. 3, 2002.

FIELD OF THE INVENTION

The invention concerns a stand for a surgical microscope of the type having a column and pivot arm mounted on the column by a rotary bearing, wherein there is an electromagnetic brake for blocking the pivoting motion of the pivot arm in the rotary bearing.

BACKGROUND OF THE INVENTION

The purpose of such stands is to hold a relatively heavy microscope for an operator so that it is movable with as little resistance as possible. The joints or bearings need to be made as resistance-free as possible so as to present the user with as little resistance as possible when moving the stand or the stand arms.

If these stands are positioned on uneven floors or if torques on the stand occur as a result of changes in loads, the relevant moving parts of the stand, in particular the stand arm, exhibit a drift behavior in the unbraked state. "Drift behavior" is to be understood as lateral pivoting motions about a rotation axis, or tendencies toward such pivoting motions, by the carrier arm, which are undesirable for the user.

Drift can occur with ceiling mounts as well. It results whenever deflections occur as a result of limited rigidity of one of the horizontal stand arms, and further horizontally arranged arms or components are pivotably mounted on that stand arm.

In surgical microscopes, drifting of the stand arms about an axis is prevented by way of an electromagnetic brake. When this brake is released, however, in order to displace the stand or the microscope arranged on the stand, the moving parts of the stand can drift and the operator must exert a corresponding amount of force in order to stop that drift.

A stand for a surgical microscope having an electromagnetic brake is known from DE 101 23 166 A1. In order to optimize drift behavior when the brake is released, provision is made in the context of this stand for each individual pivot axis automatically to be held perpendicular by way of a complex mechanism. This mechanism has proven successful in practice, but its production is complex and correspondingly expensive. Especially in the case of stands for surgical microscopes which, because of their utilization, are pivoted over only very small ranges (as is the case, for example, with stands for ophthalmology), lesser requirements are imposed in terms of absence of drift in the stand.

SUMMARY OF THE INVENTION

It is therefore the object of the invention to develop a stand of the aforesaid kind in such a way that when the electromagnetic brake is released, drifting of the stand is prevented using simple means.

The invention is characterized in that a stand of the species for a surgical microscope is equipped with an additional mechanical brake. The braking force is manually adjustable and acts directly on the pivot arm in the rotary bearing. The result is that an individual adaptation of the braking force can be accomplished depending on the severity of the drift that is occurring.

In a further embodiment of the invention, provision is made for the mechanical brake to be equipped with a resiliently preloaded pin and a brake pad. The pin is on the one side joined to the brake pad, and on the other side the spring element is associated with the pin.

In a further embodiment of the invention, the pin is mounted in a hollow stem, and the spring tension is adjustable by way of a set screw that can be screwed into the hollow stem. The spring pre-tension can be varied, and the braking force thus modified, by moving the set screw.

In a further embodiment of the invention, a cup spring packet made up of several cup springs arranged one above another is provided in the hollow stem.

In a further embodiment of the invention, the hollow stem is arranged in a flange of the rotary bearing. The flange has, on the side facing toward the pivot arm, a recess for reception of the brake pad. This results in accurately fitted guidance of the pivot arm in the rotary bearing.

It has proven to be advantageous to manufacture the brake pad from bronze, in order to prevent noise upon movement of the pivot arm in the rotary bearing.

In a further embodiment of the invention, the brake pad is equipped with at least one curved surface in order to achieve an optimized braking effect.

It has proven to be advantageous to configure the surface of the brake pad associated with the pivot arm in concave fashion. The radius of the surface can be adapted to the radius of a tubular pivot arm.

In a further embodiment of the invention, the stand is embodied either as a floor stand or as a ceiling mount.

BRIEF DESCRIPTION OF THE DRAWINGS

The invention will be depicted and described in an exemplary embodiment with reference to the schematic drawings, in which:

FIG. 1 is a view of the stand;

FIG. 2 shows a portion of FIG. 1 with a pivot arm and a rotary bearing;

FIG. 3 shows a section through the pivot arm and the rotary bearing; and

DETAILED DESCRIPTION OF THE INVENTION

Figure 4:
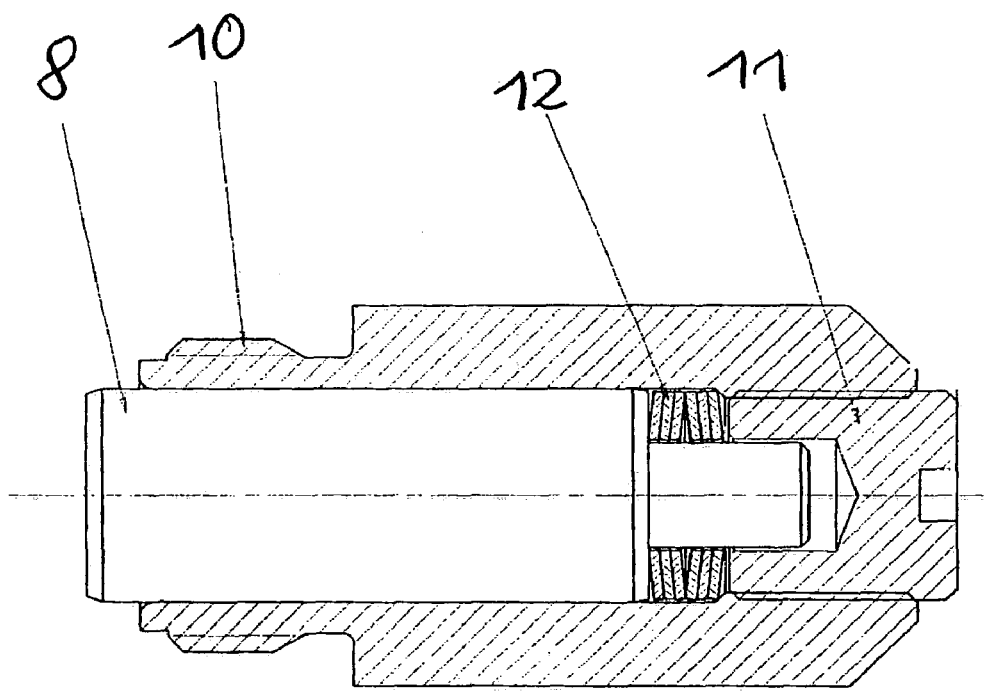
FIG. 4 is a section through a hollow stem.

FIG. 1 shows a stand 3 for a surgical microscope, having a stand foot 2, a stand column 1, and a microscope mount 17 for a surgical microscope (not depicted).

Stand column 1 is equipped with a vertical rotary bearing 4 in which a pivot arm 5 is rotatably mounted. A counterweight 16 is arranged on stand column 1 as compensation for the weight of pivot arm 5.

An electromagnetic brake 6, with which the movement of pivot arm 5 in rotary bearing 4 can be blocked, is associated with vertical rotary bearing 4. Additionally provided on stand column 1 is a flange 13 into which a hollow stem 10 of an additional mechanical brake 7 is threaded.

FIG. 2 shows an enlarged portion of FIG. 1 with rotary bearing 4 and hollow stem 10 that is threaded into flange 13. A set screw 11 is threaded onto the end of hollow stem 10.

FIG. 3 shows a section through vertical rotary bearing 4 with flange 13 and with pivot arm 5 rotatably mounted therein. Mechanical brake 7 comprises hollow stem 10 threaded into flange 13.

Hollow stem 10 is equipped in its interior with a pin 8 that is joined to a brake pad 9. Brake pad 9 is provided in a recess 14 in flange 13, and has a curved surface 15. The radius of this surface 15 is adapted to the radius of the tubular pivot arm 5.

FIG. 4 shows a section through hollow stem 10 which carries pin 8 in its interior. A cup spring packet 12 is arranged between pin 8 and the threaded-in set screw 11.

When set screw 11 is screwed in, cup spring packet 12 is compressed and force is transferred to pin 8. The latter's other end acts directly on brake pad 9 (FIG. 3) and thus on pivot arm 5 (FIG. 3).

Any drift of pivot arm 5 about the rotation axis of vertical rotary bearing 4 that occurs when electromagnetic brake 6 is released can be compensated by simply screwing set screw 11 into hollow stem 10.

PARTS LIST

1 Stand column
2 Stand foot
3 Stand
4 Vertical rotary bearing
5 Pivot arm
6 Electromagnetic brake
7 Mechanical brake
8 Pin
9 Brake shoe
10 Hollow stem
11 Set screw
12 Cup spring packet
13 Flange
14 Recess
15 Curved surface of (9)
16 Counterweight
17 Microscope mount

What is claimed is:

1. A stand (3) for a surgical microscope comprising:
   a stand column (1);
   a pivot arm (5);
   a rotary bearing (4) for mounting the pivot arm (5) on the stand column (1);
   an electromagnetic brake (6) for blocking the pivoting motion of the pivot arm (5) in the rotary bearing (4); and
   a mechanical brake (7) having adjustable braking force for braking the pivot arm (5) in the rotary bearing (4), wherein the mechanical brake (7) includes a resiliently preloaded pin (8) and a brake pad (9) connected to the pin (8) and wherein the mechanical brake further includes a hollow stem (10), a cup spring packet arranged in the hollow stem, and a set screw (11) threadably received by the hollow stem (10), the pin (8) is mounted in the hollow stem (10), and the preload on pin (8) is adjustable by way of the set screw (11), a hollow stem (10) and a set screw (11) threadably received by the hollow stem (10), wherein the pin (8) is mounted in the hollow stem (10), and the preload on the pin (8) is adjustable by way of the set screw (11), and wherein the mechanical brake further includes a cup spring packet (12) arranged in the hollow stem (10).

2. The stand (3) as defined in claim 1, wherein the rotary bearing (4) includes a flange (13) having a recess (14) facing the pivot arm (5) for reception of the brake pad (9), and the hollow stem (10) is arranged in the flange (13).

3. The stand (3) as defined in claim 1, wherein the brake pad (9) is manufactured from bronze.

4. The stand (3) as defined in claim 1, wherein the brake pad (9) has a curved surface (15) for contacting the pivot arm (5).

5. The stand (3) as defined in claim 4, wherein the curved surface (15) of the brake pad (9) is concave.

\* \* \* \* \*